United States Patent [19]

Smith

[11] Patent Number: 5,201,231

[45] Date of Patent: Apr. 13, 1993

[54] VOLUMETRIC AIR SAMPLER FOR COLLECTING MULTIPLE DISCRETE SAMPLES

[75] Inventor: Edgar G. Smith, San Antonio, Tex.

[73] Assignee: Dorothy A. Smith, San Antonio, Tex.

[21] Appl. No.: 873,597

[22] Filed: Apr. 21, 1992

Related U.S. Application Data

[63] Continuation of Ser. No. 704,667, May 20, 1991, abandoned, which is a continuation of Ser. No. 542,638, Jun. 22, 1990, abandoned, which is a continuation of Ser. No. 416,874, Oct. 4, 1989, abandoned.

[51] Int. Cl.$^5$ .............................................. G01N 31/20
[52] U.S. Cl. .................................................. 73/863.22
[58] Field of Search ..... 73/28, 863.01, 863.21–863.23, 73/863.25, 863.33, 863.83, 864.34; 55/270

[56] References Cited

U.S. PATENT DOCUMENTS

| | | | |
|---|---|---|---|
| 2,307,602 | 1/1943 | Penney et al. | 73/863.21 |
| 2,675,697 | 4/1954 | Quynn et al. | 73/863.22 |
| 3,410,059 | 11/1968 | Garnier | 73/864.34 |
| 3,475,951 | 11/1969 | Goetz | 73/28 |
| 3,518,815 | 7/1970 | McFarland et al. | 73/863.22 |
| 3,540,261 | 11/1970 | Scoggins | 73/28 |
| 3,654,801 | 4/1972 | Keefer et al. | 73/28 |
| 3,903,745 | 9/1975 | Bolser | 73/863.23 |
| 3,972,226 | 8/1976 | Rountree et al. | 73/28 |
| 4,478,094 | 10/1984 | Salomaa et al. | 73/863.32 |

Primary Examiner—Robert Raevis
Attorney, Agent, or Firm—Cox & Smith

[57] ABSTRACT

A mechanical air sample collector used to detect the presence of airborne impurities in ambient air. The apparatus collects volumetric samples of air in multiple discrete samples periodically, over set periods of time, without excessive supervision by an operator.

1 Claim, 2 Drawing Sheets

VOLUMETRIC AIR SAMPLER FOR COLLECTING MULTIPLE DISCRETE SAMPLES

This application is a continuation of application Ser. No. 07/704,667 filed on May 20, 1991, now abandoned, which is a continuation of application Ser. No. 07/542,638 filed on Jun. 22, 1990, abandoned, which is a continuation of application Ser. No. 07/416,874 filed on Oct. 4, 1989, now abandoned.

BACKGROUND OF THE INVENTION

This invention relates generally to mechanical air sample collectors used to detect the presence of airborne impurities in ambient air and, more particularly, but not by way of limitation, to volumetric air samplers that collect multiple discrete samples periodically, over set periods of time, without supervision.

Air sampling to determine the contents of an airborne environment is important to determine if microscopic objects of medical and/or biological interest, both vegetable and mineral, are present in the air in a given location. Among objects to be collected, most important are airborne pollens, fungal spores and other objects of interest to allergists, other physicians, botanists and plant pathologists. Furthermore, for various purposes which will become apparent in the following disclosure, it is important to determine at what periods of the day such objects are released into the air.

A conventional air sampling device can only collect one large sample over its normal sampling period. Although the sampling period can be varied in length, only one sample can be obtained. One such machine takes a sample for one minute out of every ten minutes in a 24-hour period, which produces a cumulative sample composed of 144 smaller samples laid down one on top of the other. As there is no way to know at what time any of these objects were collected, the volumetric count is simply an averaged count expressed as a number per cubic meter for each of the objects collected.

Samples collected by the above method are laid down on top of each other and, thus, periods of high object counts followed by an extended period of little or no release of objects from trees and fungi causes the larger number collections to be diluted and averaged along with smaller or zero counts from subsequent and previous sampling periods. The resulting average number does not reflect an accurate picture of what precisely happened in the test environment during the 24-hour period. The times of the day when counts that were high enough to produce pronounced allergic symptoms in sensitive persons, or which threatened the health of particular plants, cannot be isolated.

Another currently available device takes single samples every hour on conventional reading devices such as normal laboratory slides. However, this machine is limited by the fact that the operator using it must time the sampling period hourly and constantly reset the machine "on" and "off" every hour. This allows collection of only one sample every hour and must be constantly and tediously attended to by an operator.

Another available device takes a continuous sample on sticky tape attached to a rotating drum. The sampling period can be one to seven days, depending upon the setting of the machine. The resulting samples collected with this machine, again, reflect only an average volumetric count for the period, which makes it impossible to determine at what specific time of day the high concentration of the objects were released into the test environment. Furthermore, preparing the sticky tape for microscopic examination to determine the number of objects collected can present serious problems if the operator lacks the necessary dexterity and training.

Trees, weeds, grasses and other plants that produce pollen and fungi that produce spores do not release same continuously, and some do so only for short periods of time. Each variety may only release once each day at quite different times during a 24-hour period. Although some release randomly throughout the day, others are more consistent in their behavior. Some trees release pollen only during daylight hours, while others may do so during the hours of darkness. The same is equally true of other plants and various fungi. For this reason, random sampling or taking of only a few arbitrary samples each day may completely miss a high pollen or mold count.

It is useful to know at what times of the day various plants and fungi released large quantities of pollen or spores so that they may be related to the allergic symptoms of those whose reactions began at about the same time of day. The frequency with which this invention is able to take discrete samples, identifiable as to time, makes detection of such surges almost certain. This information is useful in providing treatment for patients whose allergies are known and may provide important clues as to the allergens affecting patients whose allergies have not been identified.

The present invention overcomes the shortcomings of the prior art by providing a volumetric air sampler that can collect multiple discrete samples of microscopic objects over set periods of time with minimal supervision at frequencies determined and programmed electronically by an operator.

The present invention allows volumetric counts of objects at given time periods. This, in turn, is a good reflection of the air concentration of these objects at that particular time. Since the volume of air sampled at a given and discrete period is known, the count is easily converted to the number contained in a cubic meter or other volumetric measure of air. High counts are associated with various human, animal and plant allergies and associated diseases, while low counts are considered with less significance.

Taking multiple discrete samples has not been possible until the present invention because no means existed for moving a laboratory slide in precise increments and in a precise relationship with an air source. There is a need for an apparatus by which a laboratory slide can be moved precise increments, combined with an accurate timing device which provides multiple discrete samples identifiable as to the day and time at which they were collected.

The present invention provides these unique advantages that were not available in the relevant market prior to this disclosure. These and other novel advances provided by this disclosure will be apparent to those skilled in the art in the following Summary of the Invention.

SUMMARY OF THE INVENTION

The present invention (hereinafter "SAMPLAIR") is a highly efficient, volumetric air sampler that collects multiple discrete samples on reading devices, such as ordinary laboratory slides, according to a programmed cycle established by the user. The samples collected are thin strips in the range of 0.550 to 0.675 inch in length and in the range of 0.035–0.040 inch in width with 2 mm from the center of one sample to the center of the next.

Although it is possible to take hundreds of samples every 24 hours, using a conventional laboratory slide determines the number of times the slide must be changed and the frequency with which the machine must be attended. Thus, the preferred practical sampling number to collect readable and accurate samples is ordinarily 24. Although the invention can be modified to use a reading device other than a conventional laboratory slide, no simpler or more efficient device is presently available for general use.

SAMPLAIR operates on 110/120-volt AC normal house current converted to 12-volt DC by an adapter. The invention can be used indoors to detect impurities in the home or office, and in remote areas that lack electricity by using a 12-volt DC power source such as a solar-charged battery pack. The battery pack can also be a rechargeable power source using a 12-volt DC adapter plugged into a regular 110/120-volt AC outlet. Other alternate means of providing power will be apparent to those skilled in the art.

SAMPLAIR can be programmed to take a number of samples per day that will permit the user to leave it unattended for a number of days. For instance, by taking eight samples a day, the machine can be left unattended for three days, or by taking six samples a day, it can remain unattended for four days. Because the time of collection of the first and last samples is known, it is a simple matter to determine the day and time at which all of the samples were collected.

The apparatus of the present invention offers great advantages to doctors, technicians and other users who are unable to attend to it on weekends or at other times when their facility is closed. As this sampler will take up to 24 samples on a single laboratory slide, programming it to take eight (8) per day will permit the user to leave it unattended, for example, over a weekend and have an adequate number of samples for each day over the weekend until the slide is replaced on the following Monday. Again, because the time interval between samples is known, as are the times at which the first and last samples were taken, it is a simple matter to identify the samples as to day and time.

SAMPLAIR exceeds, over other devices available in the relevant market, the number of objects that can be accurately collected in a given time period. The disclosure submitted herein relating to the volume of air sampled, measured in liters of air-per-minute, can be easily verified by long-established laboratory methods used to measure air flow. This is in contrast to other air sampling devices currently marketed which use methods of sampling that preclude measurement of the volumes of air sampled. Counts produced from samples taken by this invention are, therefore, extremely accurate and much more useful for scientific studies that require highly accurate counts.

SAMPLAIR used indoors is simple enough to operate that a patient with allergies can be trusted to take it home and use it to collect periodic samples in various parts of his house. It is also the ideal sampler for those who specialize in the analysis of "sick buildings" and other locations that appear to produce unusual amounts of hypersensitive reactions and other related symptoms among exposed persons.

Because SAMPLAIR can also be operated for days on power provided by rechargeable battery packs such as solar collectors, it can be used in areas where normal house current is not available. It can be placed among row crops on farms to sample for disease-causing fungi, in remote areas to sample for marijuana pollen in order to track down illegal growths, and in mountainous regions, forests, deserts and other remote locations for scientific research. This invention operates in exactly the same way on battery power as it does on house current, and samples at the same rate. It will perform indefinitely, as long as there is a sufficient power source to maintain the required operating voltage. The attendance by the user is required only when a slide must be changed or when a change in the sampling cycle is to be reprogrammed.

Other objects, features and advantages of the invention will become evident in light of the following detailed description considered in conjunction with the referenced drawings of the preferred exemplary embodiments according to the present invention.

BRIEF DESCRIPTION OF THE DRAWINGS

FIG. 1 also depicts one embodiment which uses an AC power source adapter.

DETAILED DESCRIPTION OF THE PREFERRED EMBODIMENT

Figure 1:
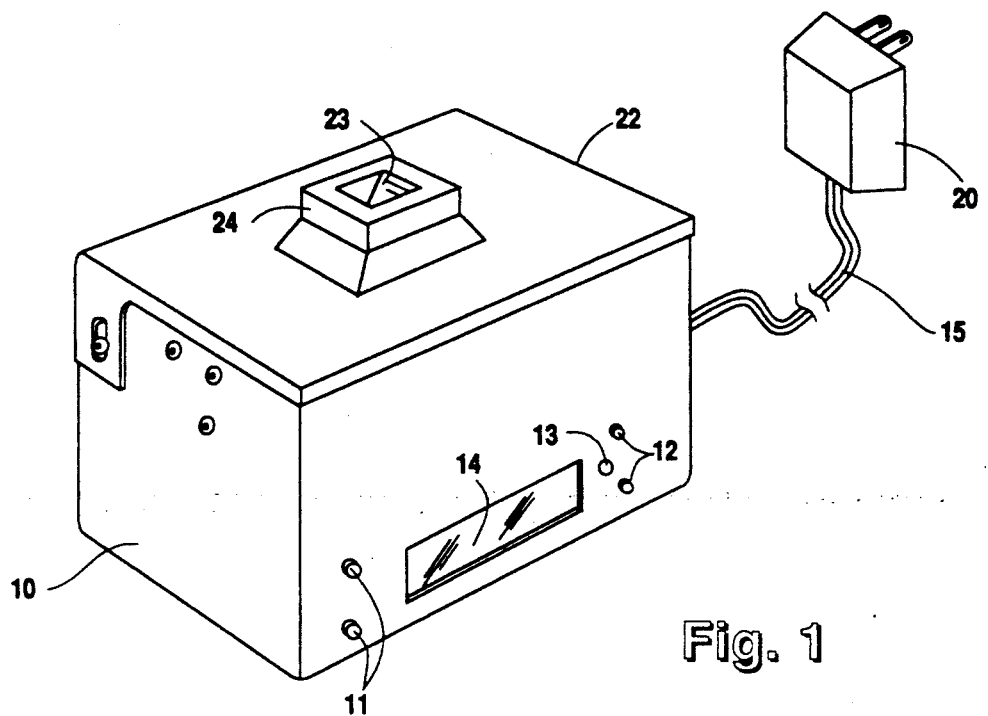
FIG. 1 is a perspective view of the invention showing the total apparatus in production and marketable form.

FIG. 1 depicts a production model of SAMPLAIR. The entire invention is housed in box 10. SAMPLAIR's external electronic controls "on" buttons 11 and "off" buttons 12 are used to program the unit for variable sampling to collect periodic, discrete air samples according to the frequency and duration desired by the operator. Such electronic circuitry and electronic control means are well-known to those skilled in the art. Programming is facilitated by an LCD display 14 which gives visible readings in numerals indicating time settings.

SAMPLAIR can be powered by a variety of power sources including, as depicted in FIG. 1, a 110/120-volt AC adapter 20. A 12-volt power supply can be substituted with minimal effort to be used in places where AC outlets are not available. Such devices well-known to those skilled in the art include, but are not limited to, automobile batteries, rechargeable and ordinary DC batteries, solar packs, and wind-generated sources of electric energy. FIG. 1 further depicts a closed hinged lid 22 upon which is molded chimney 24, down through which air is drawn and then passed through aperture 23, allowing samples of air to be collected.

Figure 2:
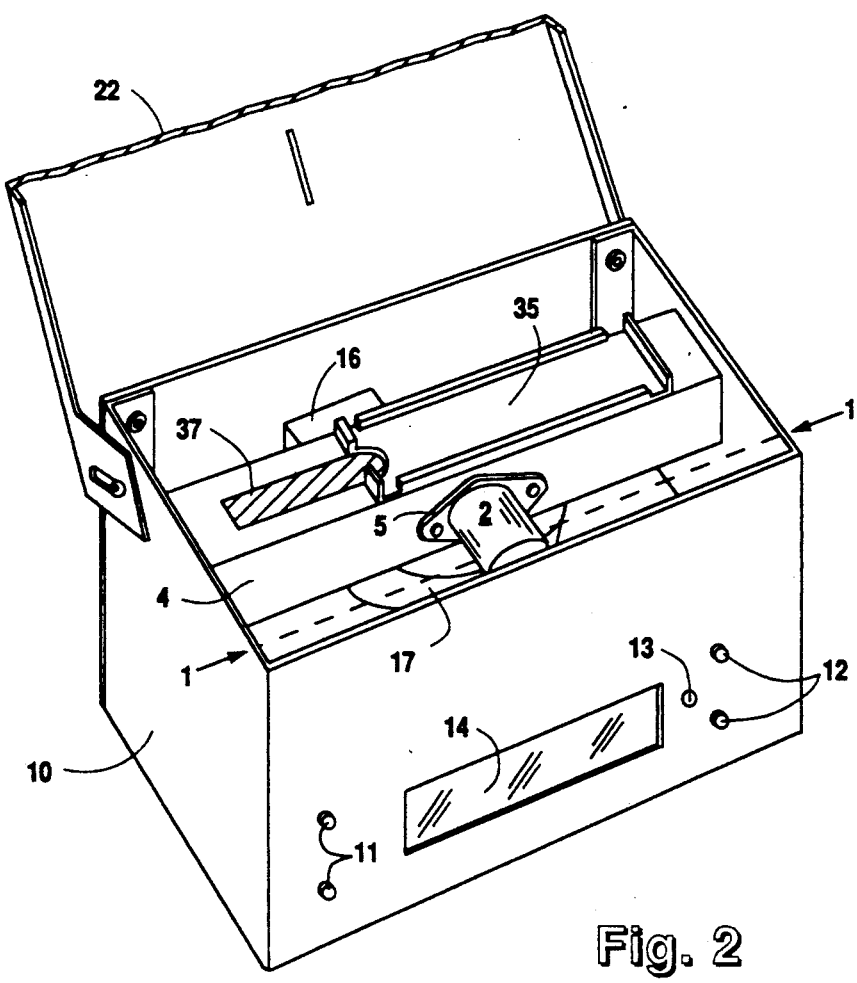
FIG. 2 shows a top view of a preferred embodiment of the SAMPLAIR unit with its hinged lid raised to permit view of the internal mechanics.

Referring to FIG. 2, lid 22 is shown in an open position. The internal mechanism which comprises the preferred embodiment is shown from a top-perspective view. Mounted lengthwise across the inside of box 10 is supporting beam 4 which supports stepper motor housing 5 and contains track slot 37. Stepper motor housing 5 contains stepper motor 2. Resting within slot 37 is a laboratory slide holder tray 35.

Figure 3:
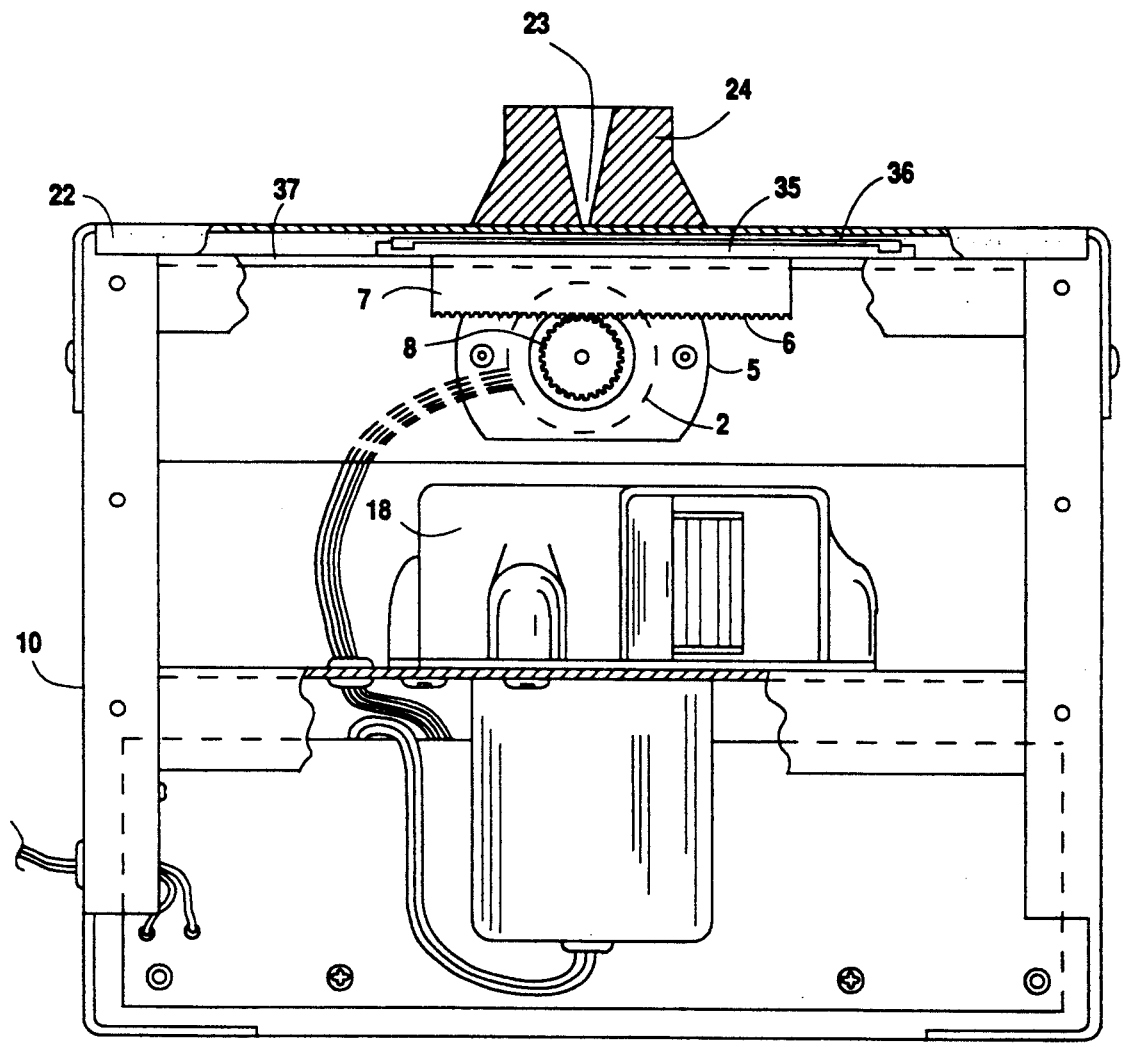
FIG. 3 is a cut-away lengthwise view of the SAMPLAIR unit depicting the preferred embodiment showing a side view of the internal workings.

The phantom line depicted between numerals 1 and 1 is the lengthwise cut-away line along which the cross section depicted in FIG. 3 is shown. Referring to FIG. 3, samples are collected on a greased laboratory slide 36 which is carried in tray 35. A conventional laboratory slide is 75 mm long, and tray 35 is, accordingly, approximately 76 mm long to hold the conventional slide 36 snugly in place. Slide 36 which is carried in tray 35 moves in a series of 2-mm steps along slotted track 37. To obtain realistic samples with sufficient, distinct clarity without overlapping with the next adjacent sample collected at another period, the samples should be at minimum 2 mm from the center of one sample to the center of the next. The total number of samples that can be taken on a single slide 36 are twenty-four, a limitation imposed by the length of the slide 36 and the practical and distinctive samples that can be collected.

The number of samples actually taken in a 24-hour period is dictated by the program established electronically by the user. Referring to FIG. 2, programming is carried out by setting "on" buttons 11 and "off" buttons 12 on each side of the front panel of box 10. "On" time is set by using the minute and hour buttons 11, and "off" time is set by using similar buttons 12. The times selected are shown on the LCD display window 14 located between said buttons.

Referring back to FIG. 3, tray 35, which carries laboratory slide 36, has a rack 7 attached to its underside. Rack 7 has at its underside a plurality of teeth 6. Rack 7 projects through the slotted track 37 on which the tray 35 rides so that said plurality of teeth 6 matchingly engage gear 8 mounted on the shaft of a stepper motor 2. Rotation of the gear 8 by the stepper motor 2 will cause rack 7 to move an equal distance along the track 37. The tray 35 which is attached to rack 7 moves the same equal distance, thus moving the greased laboratory slide 36, which is fitted snugly onto tray 35, an equal distance along the track 37.

Gear 8 and rack 7 were selected and matched so as to move the tray and greased slide 36 two millimeters each time a sample is taken. The distance from the center of one sample to the center of the next is, thus, two millimeters, and provides for adequate clear space between the samples for accurate microscopic reading.

Tray 35 carries slide 36 directly under aperture 23 when lid 22 is closed. Aperture 23 is 0.040 inch in width and 0.563 inch in length; thus, the samples collected on slide 36 are in similar ranges. In the preferred embodiment, slide 36 is capable of accepting twenty-four samples, each of which measure in the range of 0.035 to 0.040 inches or 0.889 millimeters in width and 0.550 to 0.675 inches, or 17,145 millimeters in length. Samples can be increased in length by approximately 0.125 inch, but increasing the width results in cluttered conditions which is practically not desired. In the preferred embodiment, the above stated width ranges provide clear and defined areas of separation between samples on the collection slides. Although changing dimensions simply requires making a change in the size of the aperture 23, this in turn affects the volume of air processed and the number of objects captured from the air. In general, such variations have been found to have a negative effect.

Sampling occurs when the electric blower 18 is turned on at the same time the slide 36 is advanced by the stepper motor 2. The blower 18 draws air through the aperture 23, causing the sample of air to impact the greased slide 36 and to deposit the microscopic objects carried on the air current onto the greased surface. Because of the powerful wind created by the blower 18, a large number of objects are collected and the sample is clearly seen as a thin, colorless strip on the grease. As the samples accumulate, they appear as evenly spaced strips, side by side, with clear spaces therebetween.

When the operator is ready to read the samples, it is only necessary to insure that the machine will not be taking another sample in the next two or three minutes. The operator raises the lid 22, removes the slide 36 containing desired samples and places another greased slide in the tray 35 and returns the tray back along slot 37 to the point where sampling is to begin again. This allows for continuous sampling operations. The existing program sampling cycle will continue until changed by the user. The removed slide containing the collected samples is prepared using laboratory techniques well-known in the art and read on a conventional microscope well-suited to accept said slide, and the objects collected are identified, measured and counted.

Although other types of collecting surfaces might be adapted in lieu of laboratory slides, such as linear glass rods, the standard laboratory slide 36 is much more conveniently available. Most users of SAMPLAIR already possess conventional laboratory microscopes. Conventional laboratory microscopes are designed to accept standard laboratory slides such as used in the preferred embodiment, and using alternate collecting surfaces will cause difficulty because additional equipment not readily available will have to be purchased. All known alternative reading surfaces are more difficult to use because of the difficulty of procedure and consequent training of personnel to carry out such procedure. Nothing else known is easier to use with the apparatus of this invention than the conventional laboratory slide.

Other modifications of the preferred embodiment include the collection of fungal spores on agar culture plates; the use of additional tracks to make possible the collection of samples over a much longer period of time; and the use of shorter blower motors to lower the height profile of box 10 to permit its introduction into restricted areas too small for the present production model to enter. The preferred embodiment contains electronic circuitry that will make it possible for modifications to program variable sampling periods and take more samples in one period than in another.

Thus, the present invention is well-suited to carry out the objects and attain the ends and advantages mentioned above as well as those inherent therein. While the preferred embodiments of the present invention have been described for the purposes of this disclosure, changes in the design and arrangements of features can be made by those skilled in the art, which changes are encompassed within the spirit of this invention as defined by the appended claims.

What is claimed is:

1. An apparats for automatically collecting multiple discrete airborne particles at up to 24 preselected intervals, comprising:

a box-like enclosure having an open top and a hinged lid closing said open top;

means defining a pair of spaced horizontal parallel tracks adjacent the top of said box;

a microscope slide holder mounted on said tracks for horizontal movements along said tracks;

means on said slide holder for securing a microscope slide in a horizontal position thereon, said microscope slide having a length dimension parallel to said slide holder movements and capable of receiving 24 separate deposits of airborne particles having a width on the order of 1 mm. and spaced apart by at least 2 mm.;

a rack secured to said slide holder in depending relation and projecting downwardly between said tracks;

said rack having horizontally extending gear teeth formed on the bottom surface thereof;

an electric stepping motor fixedly mounted in said box and having a horizontally disposed output shaft extending adjacent and transverse to said rack gear teeth;

a pinion affixed to said motor output shaft and drivingly engaged with said rack gear teeth;

manually setable electrical control means for energizing said stepping motor at up to 24 selected intervals, but only for a period sufficient to cause said slide holder to move along said track by a distance not less than 2 mm.;

means on said lid defining a restricted, generally rectangular, aperture overlying the path of said slide holder and communicating with ambient air, the length axis of said aperture being perpendicular to the movement of said slide holder;

an electric motor operated blower mounted within said box and having an inlet positioned to draw ambient air into said box through said aperture; and control means for energizing said blower motor only during each preselected interval.

* * * * *